United States Patent [19]

Osaki et al.

[11] Patent Number: 4,849,623

[45] Date of Patent: Jul. 18, 1989

[54] SYSTEM AND METHOD FOR DETERMINING ANISOTROPY OF LIGHT-TRANSMITTING SHEET SPECIMEN

[75] Inventors: Shigeyoshi Osaki, Hyogo; Kiyokazu Sakai, Nishinomiya; Yoshihiko Fujii, Osaka, all of Japan

[73] Assignee: Kanzaki Paper Manufacturing Co., Ltd., Tokyo, Japan

[21] Appl. No.: 945,776

[22] Filed: Dec. 23, 1986

[30] Foreign Application Priority Data

Dec. 30, 1985 [JP] Japan .................................. 60-297490

[51] Int. Cl.$^4$ .......................... G02F 1/01; G01B 11/18
[52] U.S. Cl. ...................... 250/225; 356/35; 356/368
[58] Field of Search ................ 250/225; 356/368, 367, 356/366, 370, 33, 34, 35

[56] References Cited

U.S. PATENT DOCUMENTS

| | | | |
|---|---|---|---|
| 3,293,908 | 12/1966 | Chapman | 356/33 |
| 3,679,309 | 7/1972 | Hiragaki et al. | 356/368 |
| 3,724,952 | 4/1973 | Vossberg | 356/368 |
| 3,902,805 | 9/1975 | Redner | 356/35 |
| 4,118,125 | 10/1978 | Gundermann | 356/368 |
| 4,140,902 | 2/1979 | Young | 250/225 |
| 4,171,908 | 10/1979 | Robert et al. | 356/366 |
| 4,410,277 | 10/1983 | Yamamoto et al. | 356/366 |
| 4,581,575 | 4/1986 | Osaki et al. | 324/58.5 A |
| 4,619,681 | 10/1986 | Tetaz et al. | 356/35 |
| 4,684,256 | 8/1987 | Tsumura et al. | 356/366 |

FOREIGN PATENT DOCUMENTS 0936125 7/1948 France ................................. 356/33

OTHER PUBLICATIONS

Boyarskaya et al, "Investigation of the Hardness Anisotropy of Crystals Using Polarized Light", *Institute of Appl. Physics*, vol. 36, No. 8, 8/70, pp. 989–992.
*Professor Coker's Photo–Elastic Apparatus*, Adam Higler Ltd., 5/31 pp. 1–31.

Primary Examiner—David C. Nelms
Assistant Examiner—Michael Messinger
Attorney, Agent, or Firm—Morgan & Finnegan

[57] ABSTRACT

A system and method for determining the anisotropy of a sample of a light transmitting sheet is disclosed. The surface of the sample is irradiated with a polarized light which is directed through the sample to an analyzer element. The polarizing plane of the analyzer is matched to, or maintained in a predetermined angular relation to, the polarizing plane of the polarized light. The sample is rotated relative to the analyzer element so that the optical anisotropy can be determined from the relationship between the rotation angle and the output of measured light.

15 Claims, 3 Drawing Sheets

A: AMPLITUDE OF INCIDENT LIGHT
x: AN OSCILLATING DIRECTION OF LIGHT WAVE
y: THE DIRECTION PERPENDICULAR TO x

V: LIGHT INTENSITY OBSERVED THROUGH AN ANALYZER HAVING THE MATCHING POLARIZING PLANE

V¹: LIGHT INTENSITY OBSERVED THROUGH AN ANALYZER HAVING THE CROSSING POLARIZING PLANE

4,849,623

SYSTEM AND METHOD FOR DETERMINING ANISOTROPY OF LIGHT-TRANSMITTING SHEET SPECIMEN

TECHNICAL FIELD

The present invention relates to a system for measuring optical anisotropy of optically transparent or translucent films or sheets.

BACKGROUND ART

Conventionally, a wide variety of light-transmitting dielectric sheets are manufactured by factories. For example, anisotropy of any plastic sheet normally emerges itself by elongation applied during molding process to cause the film tensile strength to eventually vary according to the rate of elongation applied, or the anisotropy emerges from the thermal deformation during heating process due to varied thermal expansion coefficient caused by directional factors. Consequently, in order to securely stabilize dimension, orientation of plastic molecules making up a film should strictly be controlled. Conventionally, molecular orientation of plastic film is checked by either X-ray diffraction pattern, infrared dichroism, or by measurement of the aspect ratio of the dynamic strength. However, any of these conventional methods needs a considerable time for correctly determining the orientation characteristic. Furthermore, it is difficult for any of these conventional systems to quickly detect whether the aimed orientation is securely achieved during film molding process, or not, before advising manufacturing staff of the checked result to allow them to correctly control the orientation. As a result, all the concerned keenly look forward to an early implementation of a novel system capable of easily and quickly checking and confirming the orientation of dielectric sheets.

SUMMARY OF THE INVENTION

The primary object of the present invention is to provide a novel method and device capable of easily and quickly implementing optical measurement of the molecular orientation of dielectric sheets, in particular, transparent or translucent sheets.

In one aspect of the invention to securely achieve the above object, the system for determining anisotropy of light-transmitting sheet specimen first causes polarized light to penetrate through either a dielectric sheet or film as specimen and then measures the light transmitted through the specimen by using an analyzer. Then the system maintains a fixed angular relationship between the incident polarized light and the analyzer while causing the relative rotation between the incide polarized light and analyzer, and the specimen sheet or film in order that optical anisotropy of the specimen can eventually be determined by the relationship between the rotation angle and the output of measured light. The above and other objects as well as advantages of the present invention will be better understood from the following detailed descriptin and the accompanying drawings.

DESCRIPTION OF THE PREFERRED EMBODIMENTS

Before describing the preferred embodiments of the present invention, vector diagram denoting the principle of measurement and pattern denoting the transmitted light intensity are explained below. According to the present invention, anistropy of any dielectric sheet is measured to be a difference of absorption coefficient caused by polarizing direction, and optical birefringence characteristic.

Figure 1:
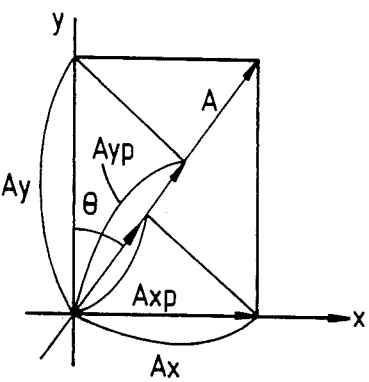
FIG. 1 is the vector diagram explaining the principle of the method related to the present invention.

Referring now to FIG. 1, assume that x denotes an oscillating direction of light wave provided in the specimen, which may be the same direction with extrusion molding of the specimen sheet, whereas y denotes the direction perpendicular to x, and plane surface xy is in parallel with the surface of specimen. Light transmitted through the specimen sheet is dissolved into polarized lights in the directions x and y by providing angle $\theta$ in which polarization of linearly-polarized-light vertically entering into the specimen surface takes place in the direction y (i.e. in the direction of electric field) and also by providing amplitude A of the incident light. By applyiing this transmitted light, when denoting the amplitude of polarized light in the direction x to be Ax and the amplitude of polarized light in the direction y to be Ay, these amplitudes can be determined by equations shown below.

$$Ax = \alpha A \sin \theta \quad (1)$$

$$Ay = \beta A \cos \theta \quad (2)$$

where "$\alpha$" denotes the amplitude transmission factor of polarized light in the direction x of specimen sheet, while "$\beta$" also denotes the amplitude transmission factor of polarized light in the direction y. The relationship of these is simply denoted to be $\alpha = \beta - 1$ in FIG. 1.

When observing the specimen transmitted light denoted by the above equations through an analyzer having a specific polarization direction identical to that of the light incident upon the specimen sheet, the light out of the analyzer contains the synthesized components of the x-directional polarized light Ax and the y-directional polarized light Ay being oriented in the direction of the analyzer. These components are denoted by equations shown below.

$$Axp = Ax \sin \theta = \alpha A \sin^2 \theta \quad (3)$$

$$Axp = Ay \cos \theta = \beta A \cos^2 \theta \quad (4)$$

Velocity of polarized light in the directions x and y in the specimen sheet, i.e., the refractive index of the polarized light, differs from each other, and as a result, there is a specific phase difference called δ between Axp and Ayp. The amplitude Ap synthesized by two light waves having the phase difference δ is determined by the equation shown below.

$$A^2p = (Axp)^2 + (Ayp)^2 + 2Axp \cdot Ayp \cos \delta \quad (5)$$

Substitution of equation 5 with equations 3 and 4 is as follows:

$$A^2p = A^2(\alpha^2 \sin^4 \theta + \beta^2 \cos^4 \theta + \tfrac{1}{2}\alpha\beta \sin^2 2\theta \cos \delta) \quad (6)$$

Figure 2:
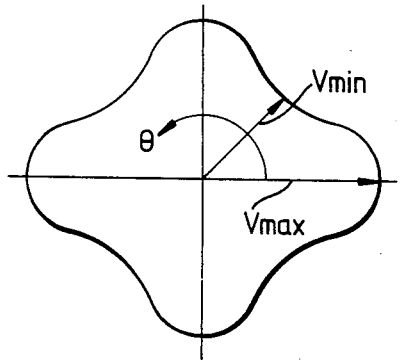
FIG. 2 is the schematic diagram denoting pattern of the light intensity transmitted through specimen varied by direction of specimen when the polarizing direction of polarized light and an analyzer correctly match.

Since the square of the light amplitide represents the light intensity, while varying the value of $\theta$ in equation (6), when causing the relative rotation between the specimen sheet and the analyzer with the polarizing plane being matched to the polarizing plane of the light incident upon the specimen, by effect of equation (6), the light intensity transmitted through the analyzer can generally be exhibited into the form as shown in FIG. 2. Value Ap can be calculated by entering values of $\theta = 0$, ]/4, and $\pi/2$ into equation (6).

$$\theta = 0, \quad A^2p = \beta^2 A^2 \quad (7)$$
$$\theta = \pi/2, \quad A^2p = \alpha^2 A^2 \quad (7')$$
$$\theta = \pi/4, \quad A^2p = [1/4(\alpha^2 + \beta^2)1/2\alpha\beta\cos\delta]A^2 \quad (7'')$$

The left-sides of the above equations (7)–(7'') correspond to the value of measured light intensity, and thus, values of $\alpha$, $\beta$ and $\cos \delta$ can be calculated from the values of measured light intensity in conjunction with $\theta = 0$, $\pi/4$, and $\pi/2$, respectively. Coefficients $\alpha$ and $\beta$ respectively denote the light-transmission factors of the specimen sheet. Result of an investigation proves that most of plastic specimen sheets have the value $\alpha^2 = \beta^2$ except for uniaxially elongated polyester which proves to be $(\beta/\alpha)^2 \approx 0.7$. Depending on the thickness of the specimen sheet, value of $\cos \delta$ is variable in a range from $-1$ to $+1$. Next, a consideration is given to a case of observing the light transmitted through a specimen sheet via an analyzer which has a polarizing plane perpendicular to that of the incident light. Assume that the amplitude of light transmitted through the analyzer is Av, the following equation is provided.

$$Av^2 = A^2 \sin^2 2\theta[\tfrac{1}{4}(\alpha^2 + \beta^2) - \tfrac{1}{2}\alpha\beta \cos \delta] \quad (8)$$

Figure 3:
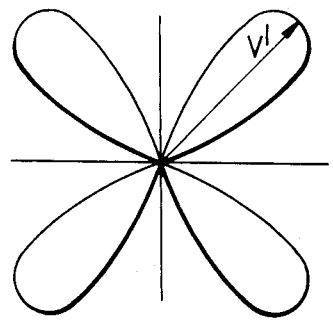
FIG. 3 is a diagram denoting variation of the light intensity transmitted through specimen caused by the direction of specimen when the polarizing directions of polarized light and analyzer cross at right angles to each other.

Diagrammatically illustration of equation (8) by applying the same manner as that of FIG. 2 generates a four-leaf like shape like the one shown in FIG. 3. Note that, as is clear from equation (8), since the transmission factor and cos δ cannot independently be calculated, actually, value is quite negligible. In conjunction with the anisotropy of the specimen sheet, since values of $\alpha$ and $\beta$ are equal to each other in many cases, cos δ itself makes up an important factor for implementing measurement. Assume that refractive index of the specimen sheet against the polarized light in the direction of x is n1, refractive index of the specimen sheet against the polarized light in the direction y is n2, thickness of the specimen sheet is d, and light wave length is λ, respectively, then the following equation can be provided.

$$\delta = \frac{2\pi}{\lambda} d(n1 - n2) \quad (9)$$

Consequently, the value (n1−n2) can be calculated from the value of cos δ by prelimirarily measuring the thickness d of the specimen sheet. The value (n1−n2) eventually becomes the data indicating the orientation of the specimen sheet itself.

PREFERRED EMBODIMENTS

Figure 4:
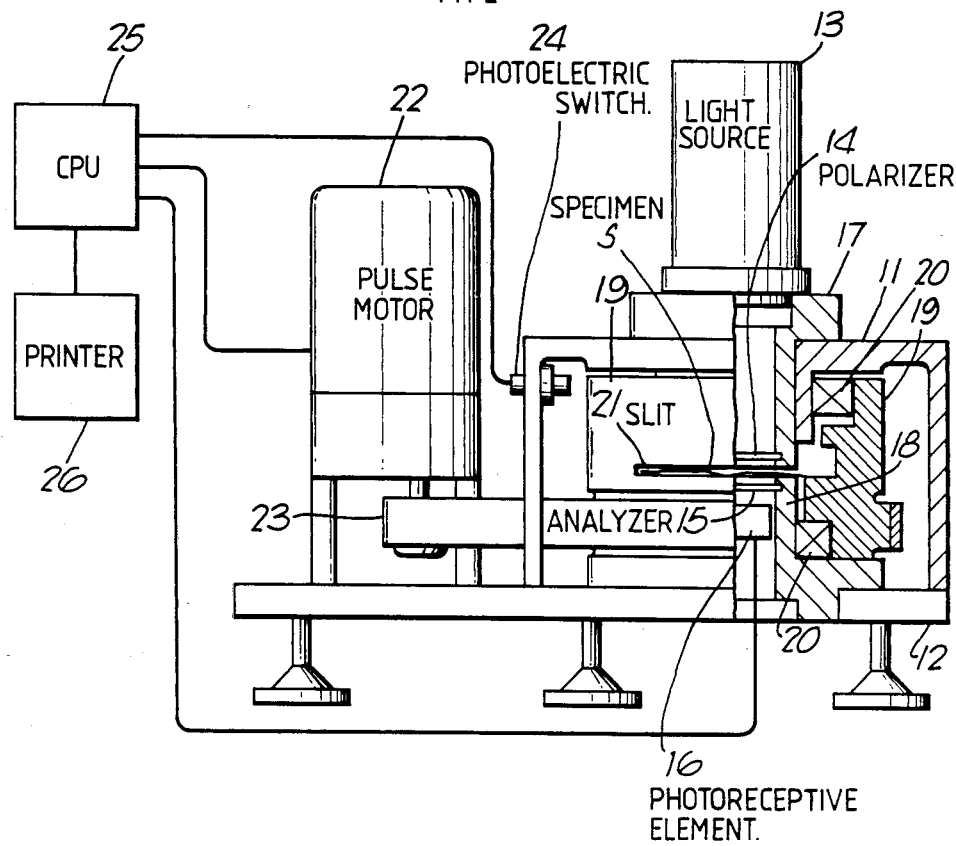
FIG. 4 is the lateral view with partial sectional view containing block diagram denoting an example of the device used for embodying the method related to the present invention by rotating a specimen.

FIG. 4 is the schematic diagram of the device 10 for determining anisotropy of light-transmitting specimen sheet in the preferred embodiment of the invention in which specimen sheet is rotated for measuring anistropy while a polarizer and an analyzer are both maintained in the predetermined fixed positions. Gate-shaped frame11 is secured to base 12, while light source 13 and polarizer 14 are respectively secured to the gate-shaped frame 11. Analyzer 15 is installed to base 12. Photoreceptive element 16 is installed below analyzer 15. The upper and lower holder cylinders 17 and 18 respectively hold polarizer 14 and analyzer 15, while these holder cylinders 17 and 18 are respectively secured to either the gate-shaped frame 11 or base 12. Specimen holder cylinder 19 is inserted into and rotatably held by the external surface of the lower holder cylinder 18, while the specimen holder cylinder 19 rotates itself pivoting on the vertically-extending cylinder portion of the frame and the lower holder cylinder 18. Bearings 20 are installed between the specimen holder cylinder 19, and the vertically-extending center cylinder portion of the gate-shaped frame 11 surrounding the upper holder cylinder 17, as well as the lower holder cylinder 18 holding analyzer 15. Specimen holder cylinder 19 is provided with slit 21 which is perpendicular to the rotating shaft at a height corresponding to the positions of and between polarizer 14 and analyzer 15. The specimen S is inserted into the specimen holder cylinder 19 via slit 21 before being placed between and in parallel with polarizer 14 and analyzer 15. Pulse motor 22 rotates the specimen holder cylinder 19 through belt 23. Photoelectric switch 24 is secured to the gate-shaped frame 11, which detects a reflective mark affixed to a specific position on the outer circumferential surface of the specimen holder cylinder 19 before generating a detect signal. Central processing unit (CPU, i.e. micro-computer) 25 controls functional operations of data processing units and related devices.

Operations of the device of the above embodiment of the present invention are described below. First, specimen film is inserted into slit 21 of the specimen holder cylinder 19 so that specimen film can securely be held by it. Operator then delivers measurement operation start-up command signal to the CPU 25 via key-board (not shown) for example. On receipt of this command signal, CPU 25 outputs pulse signals to pulse motor 22 in order to rotate specimen holder cylinder 19 in the clockwise and counterclockwise directions within a specific angular range. CPU 25 stops the operation of pulse motor 22 at the position where photoelectric switch 24 detects the reflective mark on the specimen holder cylinder 9. CPU 25 then delivers a pulse signal to pulse motor 22 so that it can rotate clockwise. CPU 25 then computes the number of pulses to detect the rotation angle of the specimen holder cylinder 19 and samples the signals output from photoreceptive element 16 per rotation of the specimen holder cylinder 19 for example, and then stores the sampled data in memory. Thus, when the specimen holder cylinder 19 makes a full turn, photoelectric switch 24 again outputs the mark-detected signal. On receipt of this signal, CPU 25 stops the operation of the pulse motor 22. Polarizer 14 and analyzer 15 are installed in order that the directions of polarization of these can correctly match to each other. As soon as specimen holder cylinder 19 completes a full turn, using equations 7 through 7" shown earlier, CPU 25 computes values of $\alpha$, $\beta$ and $\cos \delta$ from data signal output from photoreceptive element 16. Likewise, using equation 9, CPU 25 also computes value of $(n1-n2)$ from the value of $\cos \delta$. CPU 25 preliminarily stores all the data related to the thickness d of the specimen sheet and the wave length of light needed for implementing computation of these.

CPU 25 activates printer 26 to print out the ratio of $\alpha$ to $\beta$ as a result of the above computation and the result of subtraction $(n1-n2)$ and also draw a graphic curve denoting the relationship between the output data of the measured light and the rotation angle of specimen sheet shown in FIG. 2. Values of the ratio of $\alpha$ to $\beta$ and the subtraction $(n1-n2)$ respectively denote the degree of anisotropy of specimen sheet. Those measurement operations can be completed during about one minute of period. When the polarizing directions of polarizer 14 and analyzer 15 are either in parallel with or matching each other, measurement operation can be done satisfactorily. It is possible for the system to install the polarizer holder cylinder 17 at any angle ranging from 0° to a maximum of 90° or at any optional angle. Since plastic material does not cause light beams to scatter extensively, an incandescent lamp is made available for light source, thus dispensing with a monochromic filter. If the spectrum sensitivity characteristic of photoreceptive element 16 is close to the visual sensitivity, subtraction $(n1-n2)$ can be done by applying 0.5 $\mu$m of average wave length.

Figure 5:
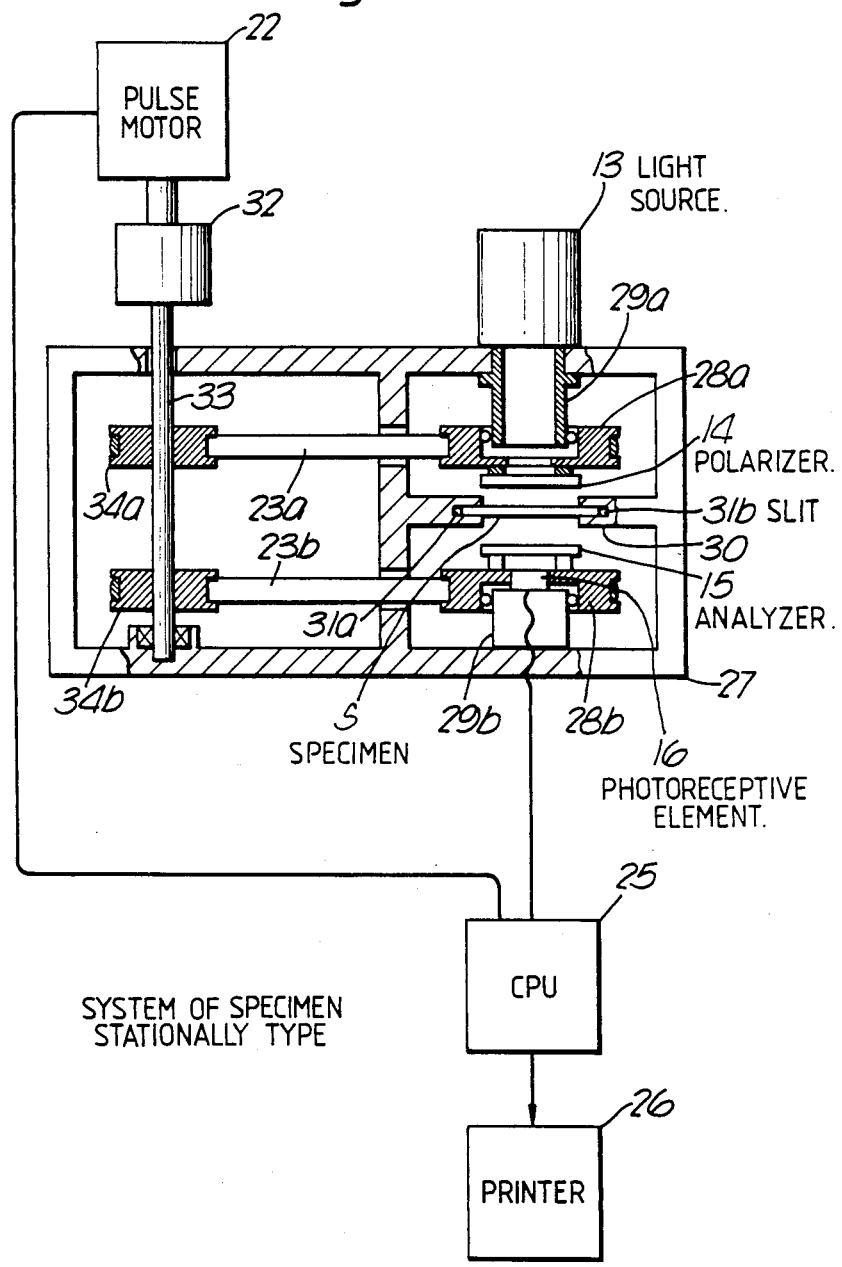
FIG. 5 is the sectional lateral view of the essential constituents containing block diagram denoting an example of the device used for embodying the method related to the present invention by rotating polarizer and analyzer relative to a stationary specimen.

FIG. 5 is the schematic diagram denoting the second preferred embodiment of the present invention with some portions similar to the portions in the embodiment shown in FIG. 4 being referred by the same numerals of the latter, in which measurement is done by synchronously rotating both the polarizer 14 and the analyzer 15 using a stationary specimen sheet without rotating it at all. Polarizer 14 and analyzer 15 are respectively installed inside of rectangular frame 27 at the upper and lower positions so that they can freely rotate themselves at an adequate distance, while these are respectively held by rotating rings 28a and 28b which are respectively held via bearings by stationary cylindrical shafts 29a and 29b being secured to the upper and lower plates of the rectangular frame 27. These rotating rings 28a and 28b respectively function as pulleys each having groove at the external circumference for supporting belts 23a and 23b. Light source 13 is installed so that it can correctly match the position of cylindrical shaft 19a, thus allowing light beams to radiate polarizer 4 through the internal space of the cylindrical shaft 29a and the bore of the rotating ring 28a. Photoreceptive element 16 is installed to the bore of the lower rotating ring 28b. To fix specimen sheet S between polarizer 14 and analyzer 15, sheet-holding member 30 is integrally or attachingly provided for the rectangular frame 27. Both sides of sheet-holding member 30 are provided with slits 31a and 31b for sequentially feeding sheet-or-web-like specimens to the test position. Belts 23a and 23b are driven by pulse motor 22 installed outside of the rectangular frame 27 via coupling 32, shaft 33, and the respective pulleys 34a and 34b secured thereon in order that the rotating force from pulse motor 22 can be transmitted to rotating rings 28a and 28b. Since pulleys 34a and 34b are provided with the same diameter, as well as those of the rotating rings 28a and 28b, polarizer 14 and analyzer 15 can synchronously or integrally rotate themselves.

The system related to the present invention not only uses those dielectric sheets made from plastic material, but it also allows use of a wide variety of sheets including texturized sheets such as wood-free paper, clay coated paper for printing, biological membrane sheets, ion-balanced composite membrane sheets, plasma-photo polymerized membrane sheets, cell sheets incorporating a variety of liquid substances inside of cells such as liquid crystal, high-polymer liquid crystal, high polymer solution, colloid solution, gelated material, short-fiber filled fluid, etc. for example. Sinsce those preferred embodiments mentioned above use light source generating non-polarized normal light beams, polarizer 14 is needed. If laser is made available for light source, since laser beams are polarized, the system does not need the polarizer, but only an analyzer is needed. Furthermore, if the thickness d of specimen sheet is constant and only the relative value of orientation should be sought as in the case of controlling film elongation process, it is not necessary to compute values $\alpha$, $\beta$ and $(n1-n2)$, but the system merely needs to draw pattern shown in FIG. 2 for determining the ratio of Vmax or Vmin.

As is clear from the foregoing description, the system related to the present invention correctly and quickly measures the anisotropy of specimen sheets when absorbing light and also measures complex refraction characteristic. The system related to the present invention provides substantial conveniences since the measurement of those factors mentioned above can easily be implemented merely by setting specimen sheets inside of the device embodies by the invention.

What we claim is:

1. A method for determining the optical anisotropy of a light transmitting sheet comprising the steps of:
   irradiating the surface of a sample of a light-transmitting sheet with a polarized light perpendicular to the surface;
   directing the light transmitted through said sample to an analyzer element with the polarizing plane of the analyzer element being matched to, or maintained in a predetermined angle relative to, the polarizing plane of said irradiated polarized light, while adjusting the angle of relative rotation between said sample and said analyzer element polarizing plane;
   directing the analyzed light from said analyzer element to a light sensor unit to generate electric signals corresponding to the light intensity detected while adjusting sais angle of relative rotation; and
   determining the optical anisotropy of said sample in accordance with the relation between the data of electric signals and said angle of relative rotation.

2. The method of claim 1 wherein the step of determining the optical anisotropy of said sample includes calculating the difference between the refractive indices of the polarized light in first and second directions in the sample plane.

3. The method of claim 1 wherein the polarized light irradiating the sample is laser light.

4. The method of claim 1 wherein the step of determining the optical anistropy of said sample includes calculating $\alpha$, $\beta$ and $\cos \delta$ by solving the equations:

for $\theta=0$, $A^2p=\beta^2A^2$ for $\theta=\pi/2$, $A^2p=\alpha^2A^2$ for $\theta=\pi/4$, $A^2p=[\frac{1}{4}(\alpha^2+\beta^2)\frac{1}{2}\alpha\beta \cos \delta]A^2$ where:
$\alpha$ = the amplitude transmission factor of polarized light in an x direction.
$\beta$ = the amplitude transmission factor of polarized light in a y direction.
A = amplitude of incident light
$\theta$ = angle of incidence of linearly polarized light
$\delta$ = phase difference between velocity of polarized light transmitted in x and y directions
$A^2p$ = measured intensity of transmitted polarized light 5. The method of claim 4 wherein $\alpha^2=\beta^2$.

6. The method of claim 4 wherein $(\beta/\alpha)^2=0.7$.

7. The method of claim 4 wherein said analyzer element has a polarizing plane perpendicular to the polarizing plane of said irradiated polarized light.

8. The method of claim 4 further comprising the step of determining the difference (n1−n2) between the indices of refraction in mutually perpendicular x and y directions in said sample plane according to the equation $$\delta = \frac{2\pi}{\lambda} d(n1 - n2)$$

where:
$\lambda$ = light wavelength
d = sample sheet thickness
n1 = sample sheet refractive index in x direction
n2 = sample sheet refractive index in y direction.

9. The method of claim 8 further comprising the step of displaying the ratio $\alpha:\beta$ and the difference (n1−n2).

10. The method of claim 1 wherein said determining step further includes determining the orientation of said sample having a substantially constant thickness of taking the ratio
TI (Vmin/Vmax)

where V is the light intensity measured through said analyzer element, said analyzer element polarization plane matching the polarizing plane of said irradiated polarized light.

11. A system for determining the optical anisotropy of a light transmitting sheet comprising:
polarized light source means;
a sample of a light transmitting sheet positioned to be perpendicularly irradiated with polarized light from said light source;
means for analyzing the light transmitted through said sample and emitted from the surface of said sample opposite to the irradiated surface, said analyzing means having a polarizing plane matched to, or maintained in predetermined angular relation to, the polarizing plane of the polarized light from said light source means;
means for supporting said sample and said analyzing means, and for adjusting the relative rotation between said sample and said analyzing means with the polarizing plane of said analyzing means being matched to, or maintained in predetermined angular relation to, the polarizing plane of the light from said light source means;
angular sensing means for establishing a reference angular position for said relative rotation;
means for controllably driving said suporting and rotation adjusting means to cause said relative rotation within a predetermined angular range from said reference angular position;
light sensing means for detecting the light transmitted through said analyzing means to generate electric signals corresponding to the light intensity during said relative rotation;
a central processing unit for referencing the state of said angular sensing means to control said driving means, and for receiving said electric signals to determine the optical anisotropy of the sample from the relation between the data of said electric signals and the angular positions in said relative rotation; and
an output device for displaying or outputting the determined optical anistropy of the sample.

12. The system of claim 11 wherein said supporting and rotation adjusting means rotates said sample relative to said analyzing means, said analyzing means being held in a fixed position.

13. The system of claim 11 wherein said central processing unit determines the optical anistropy of the sample by calculating $\alpha$, $\beta$ and $\cos \delta$ through solving the equations:

for $\theta = 0$, $A^2p = \beta^2A^2$ for $\theta = \pi/2$, $A^2p = \alpha^2A^2$ for $\theta = \pi/4$, $A^2p = [1/4(\alpha^2 + \beta^2)1/2\alpha\beta\cos\delta]A^2$ where:
$\alpha$ = the amplitude transmission factor of polarized light in an x direction
$\beta$ = the amplitude transmission factor of polarized light in a y direction
A = amplitude of incident light.
$\theta$ = angle of incidence of linearly polarized light
$\delta$ = phase difference between velocity of polarized light transmitted to x and y directions
$A^2p$ = measured intensity of transmitted polarized light.

14. The system of claim 13 wherein said analyzer element has a polarizing plane perpendicular to the polarizing plane of said irradiated polarized light.

15. The system of claim 13 wherein said central processing unit further determines the difference (n1−n2) between the indices of refraction in mutually perpendicular x and y directions in said sample plane according to the equation:

$$\delta = \frac{2\pi}{\lambda} d(n1 - n2)$$

where:
$\lambda$ = light wavelength
d = sample sheet thickness
n1 = sample sheet refractive index in x direction
n2 = sample sheet refractive index in y direction.

* * * * *